United States Patent [19]

Nagata et al.

[11] Patent Number: 4,913,792
[45] Date of Patent: Apr. 3, 1990

[54] FLAMMABLE-GAS SENSOR

[75] Inventors: Yasuhiro Nagata, Kusatsu; Satoru Sato, Osaka; Kiyoshi Furuya, Kasatsu, all of Japan

[73] Assignee: Daikin Industries, Ltd., Osaka, Japan

[21] Appl. No.: 295,599

[22] PCT Filed: Jul. 28, 1987

[86] PCT No.: PCT/JP87/00551
§ 371 Date: Jan. 5, 1989
§ 102(e) Date: Jan. 5, 1989

[87] PCT Pub. No.: WO89/01148
PCT Pub. Date: Feb. 9, 1989

[51] Int. Cl.⁴ .......................................... G01N 27/56
[52] U.S. Cl. .................................. 204/412; 204/426; 357/25
[58] Field of Search ............... 204/424, 425, 426, 412, 204/431, 432; 357/25

[56] References Cited

U.S. PATENT DOCUMENTS

| | | | |
|---|---|---|---|
| 4,076,596 | 2/1978 | Connery et al. | 204/1 T |
| 4,718,991 | 1/1988 | Yamazoe et al. | 204/1 T |
| 4,795,543 | 1/1989 | Stetter et al. | 204/412 |
| 4,820,386 | 4/1989 | LaConti et al. | 204/1 T |

FOREIGN PATENT DOCUMENTS

| | | | |
|---|---|---|---|
| 139289 | 12/1976 | Japan . | |
| 115293 | 10/1978 | Japan . | |
| 64760 | 5/1980 | Japan | 204/400 |
| 211352 | 10/1985 | Japan . | |

Primary Examiner—G. L. Kaplan

[57] ABSTRACT

At the surface of an insulating substrate there are provided a working electrode and an counter electrode with a set space from the working electrode and a gas-permeable, proton-conductive film with which the surfaces of the electrodes are overlaid in such a manner as to form an integrated whole with the electrodes. By applying a set voltage between the two electrodes, flammable gas which has permeated the gas-permeable, proton conductive film is made to undergo oxidation and reduction at a surface of the working electrode, and protons which have been produced thereby move toward the counter electrode in the gas-permeable, proton-conductive film, so that the concentration of the flammable gas can be measured. A reference electrode can be provided for the purpose of stabilizing potential of the working electrode. A mechanism which is described above can be applied to a gas sensor of field-effect transistor type.

3 Claims, 7 Drawing Sheets

FLAMMABLE-GAS SENSOR

BACKGROUND OF THE INVENTION

The present invention relates to a flammable-gas sensor.

Figure 13:
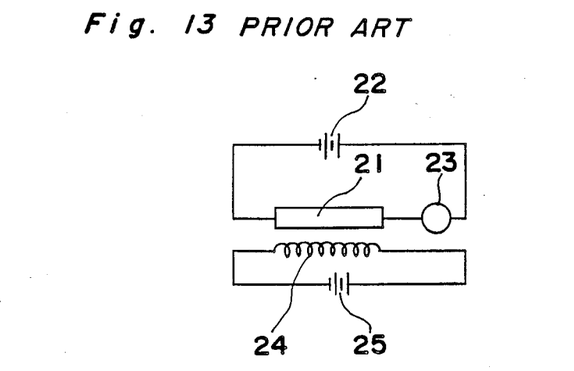
FIG. 13 and FIG. 14 each schematically illustrate a conventional flammable-gas sensor.
Figure 14:
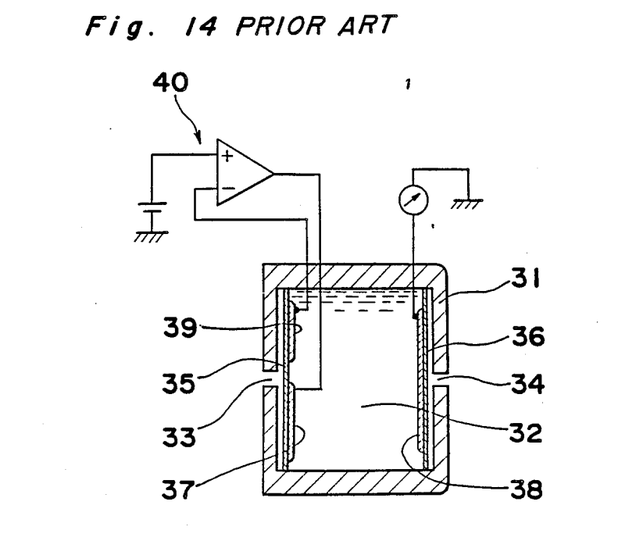

Conventionally, for a flammable-gas sensor, there has been proposed a device wherein, as shown in FIG. 13, an element 21, such as $SnO_2$, which is sensitive to flammable gases and whose resistance changes as it reacts to such gases, is arranged in series with a direct current source 22 and an ammeter 23. A heater 24 which is designed to heat said element 21 up to approximately 100° C.–400° C. is connected in series with an electric source 25. Another proposed device consists of, as shown in FIG. 14, a casing 31 which contains an aqueous solution of sulfuric acid 32 which acts as an electrolyte. The casing 31 has openings 33, 34 and is provided with gas-permeable polytetrafluoroethylene film 35, 36 at set positions inside said casing. On the inner side of said gas-permeable polytetrafluoroethylene film 35, 36 there are formed at set positions a working electrode 37, a counter electrode 38 and a reference electrode 39, all formed by a coating of platinum black. The electric potential between the working electrode 37 and the reference electrode 39 is maintained constantly by means of a potentiostat circuit 40.

Still another device proposed is a hydrogen-gas sensor of the field-effect transistor type (hereinafter abbreviated as "FET type") wherein the gate electrode of the field-effect transistor is formed of palladium (Pd).

However, problems have been involved in the operation of these devices. A flammable-gas sensor shown in FIG. 13 is designed to produce current signals corresponding to the amount of adsorption of flammable-gas particles. However, saturation of the flammable-gas particles that occurs when the adsorption reaches a certain amount renders the sensor unable to continue to detect the concentrations of the flammable gas. Furthermore, the necessity of heating up the element 21 to approximately 100° C.–400° C. by use of heater 24 in order to detect flammable gas not only makes the device complicated in design, it also may a gas explosion. Complication characterizes such a flammable-gas sensor, both in production and adjustment for use, because the element 21, influenced by production conditions, tends to result in wide variations in characteristics, and consequently, it becomes necessary to adjust the compensating circuit to the varied characteristics of the element. The electrical heating which is indispensable before a sensor becomes ready for functioning requires much time and the operation requires much electrical energy. The selectivity for detecting varieties of gases is poor; the sensor reacts similarly to flammable gases of like nature, i.e. gases such as hydrogen gas and a hydrocarbon gas. For example, a sensor, though designed to detect a leak of flammable gas, also reacts to the alcohol gas which rises from the pot when it is warmed and, in such cases, may erroneously detect such gas as a leak of flammable gas.

On the other hand, with respect to a flammable-gas sensor shown in FIG. 14, the characteristics of the gas-permeable polytetrafluoroethylene film, those of the electrodes, the accuracy of the positions of the electrodes, etc. altogether have such influences that each sensor is produced with irregularities in characteristics as a whole. The production, therefore, involves painstaking work to conform the characteristics, the accuracy of the positions, etc. to the set values. Nevertheless, it is practically impossible for each sensor produced to have uniform characteristics.

It is also a problem that the speed of the reaction, influenced by the concentration of the gas that permeates the gas-permeable polytetrafluoroethylene film, can not be substantially increased. Furthermore, with an electrolyte being contained in the casing, there is likely to occur a leakage of the electrolyte after a long period of use. The leakage impairs the reliability of a sensor in its function to detect flammable gases. This defect is conspicuous when the application is that of a portable sensor. It is virtually impracticable, therefore, to generally reduce sensors dimensionally and lower the production cost.

A hydrogen-gas sensor of the FET type is so designed that the catalytic action of palladium (Pd) causes $H^+$ ions to be formed by decomposition and to accumulate only at the gate electrode. In this method, said accumulation provides a basis for measuring the change of the concentration of hydrogen gas, but not for measuring the value of the absolute concentration.

With the problems pointed out in the above description taken into consideration, the present invention has for its object to provide a flammable-gas sensor which is satisfactory in structural simplification, in minimizing irregularities in characteristics, in improving the selectivity for flammable gases, and in ensuring a high accuracy in measurement over long periods of time.

SUMMARY OF THE INVENTION

In order to accomplish the objects stated above, according to one embodiment of the present invention, there is provided a flammable-gas sensor which comprises an insulating substrate 1, a working electrode 2 provided at a surface of said insulating substrate 1, a counter electrode 4 provided at the surface of said insulating substrate 1 within a predetermined gap from said working electrode 2, and a gas-permeable proton-conductive film 5 which covers said working electrode 2 and counter electrode 4 and forms an integrated whole with said working electrode 2 and counter electrode 4.

According to another embodiment of the present invention, there is provided a flammable-gas sensor which comprises an insulating substrate 1, a working electrode 2 provided at a surface of said insulating substrate 1, a counter electrode 4 provided at the surface of said insulating substrate 1 within a predetermined gap from said working electrode 2, a reference electrode 3 provided at the surface of said insulating substrate 1 within predetermined gaps respectively from said working electrode 2 and counter electrode 4, and a gas-permeable, proton-conductive film 5 which covers said working electrode 2, counter electrode 4 and reference electrode 3 and forms an integrated whole with said working electrode 2, counter electrode 4 and reference electrode 3.

It is preferable to form said reference electrode and counter electrode in the form of coaxial circles with said working electrode at a center.

It is also practical for said reference electrode to be positioned between said working electrode and counter electrode. It is preferable for said working electrode to be formed of a metal of the platinum group or gold and for said reference electrode to be formed of a metal which does not react with flammable gases.

It is also practical for said counter electrode to be positioned between said working electrode and said reference electrode, and for said working electrode and said counter electrode to be formed of a metal of the platinum group or gold.

It is practical for said working electrode and counter electrode, while positioned relative to each other on said insulating substrate according to predetermined arrangement, to have such dimensional relations that the counter electrode is larger in area than the working electrode by ten times or more, or preferably by 100 times or more.

In a flammable-gas sensor structurally arranged as above and with a bias given between the working electrode and the counter electrode at the surface of the insulating substrate, permeation of flammable gas through the gas-permeable, proton-conductive film to the surface of the working electrode an oxidation reaction to take place at the surface of the working electrode and an electric current proportional to the degree of the oxidation reaction to flow to the working electrode. The protons produced as a result of the oxidation migrate to the counter electrode. The proton produced as a result of the oxidation is thus prevented from remaining at the surface of the working electrode so that current signals proportional to the amount of flammable gas are always obtainable.

The same effect as above can be achieved when a working electrode, a reference electrode and a counter electrode are placed at the surface of said insulating substrate so that the potential at the surface of the working electrode can be prevented from variation by controlling the potential between the working electrode and the reference electrode. If, in this arrangement, said reference electrode and counter electrode are formed in the form of coaxial circles with the working electrode at the center, the potential between the working electrode and reference electrode can be controlled quickly and assuredly even when the influence of oxidation or reduction occurs only locally to the working electrode.

Where said reference electrode is placed between said working electrode and counter electrode, the potential between the working electrode and reference electrode can be controlled more quickly and more assuredly. Where said working electrode is formed of a metal of the platinum group or gold and the counter electrode is of a metal which does not react with flammable gases, the use of costly metals of the platinum group or gold can be decreased quantitatively, so that the cost of a sensor as a whole can thus be lowered.

Positioning of said counter electrode between said working electrode and reference electrode affects the control of the potential between the working electrode and the reference electrode which reacts to changes of the potential of the counter electrode. The ability to respond being lowered somewhat, the measurement is done with a substantially high accuracy. Especially where a metal of the platinum group or gold forms each of said working electrode and counter electrode, as compared with the use of a metal such as silver or lead that does not react with flammable gases, electrode characteristics of the counter electrode is so improved that improvement in accuracy of measurement is achieved. The use of costly metals of the platinum group can be reduced to a minimum requirement.

Where the counter electrode is larger in area than the working electrode by a factor of a two-figure number or more while said electrodes are positioned relative to each other at the surface of said insulating substrate according to predetermined arrangement, the potential at the surface of the working electrode can, by virtue of the enlarged ratio in area between said two electrodes, be rendered as stable as where a reference electrode is provided.

According to another embodiment of the present invention, there is provided a flammable-gas sensor wherein either of the gate electrode and the source electrode of a field-effect transistor is formed of a metal of the platinum group and the other electrode is formed of a metal which does not react with flammable gases while a gas-permeable proton conductive film covers both said gate electrode and source electrode and forms an integrated whole with these electrodes.

In this embodiment stated above, silver can be employed as a metal which does not react with flammable gases.

In a flammable-gas sensor structurally arranged as above, the gas-permeable, proton-conductive film permits a flammable gas to permeate therethrough to the electrode formed of a metal of the platinum group. The flammable gas, by the catalytic action of said platinum group metal, is decomposed into electrons and protons. The electrons are deposited at said electrode and the protons are allowed to freely move through said gas-permeable, proton-conductive film, which is, for example, a film of antimonic acid, zirconium phosphate, a of tetrafluoroethylene and perfluorovinyl ether, or the like, so as to be prevented from reunion with said electrons. The potential of the electrode formed of a metal which does not react with flammable gases is maintained at a set value without being influenced by the concentration of the flammable gas.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

PREFERRED EMBODIMENTS OF THE INVENTION

Referring now to drawings, there are explained in detail embodiments of the present invention, as follows.

Figure 1:
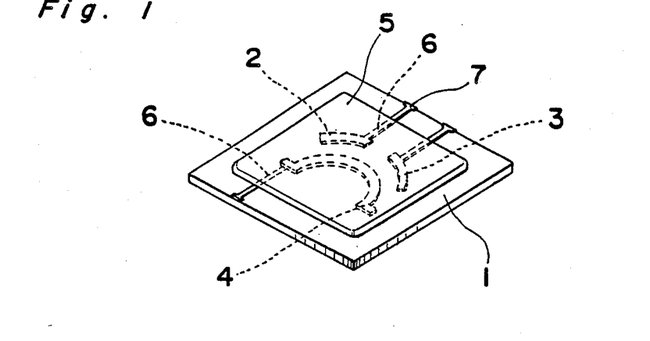
FIG. 1 illustrates an embodiment of the present invention in a schematic perspective representation.
Figure 2:
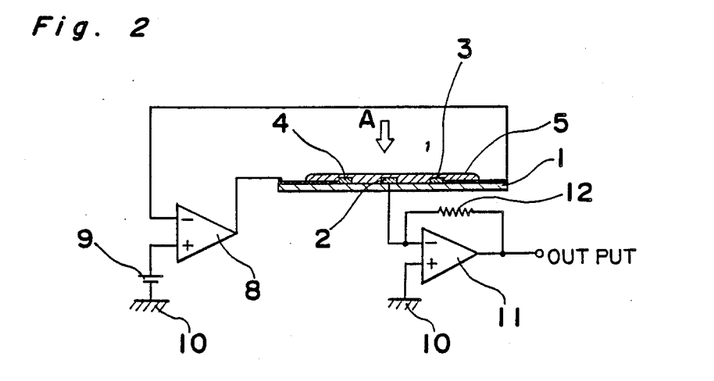
FIG. 2 is a schematic cross-sectional view of the above embodiment.

FIG. 1 shows a flammable-gas sensor embodying the present invention in a schematic perspective representation, and FIG. 2 is a schematic view of a cross section of the embodiment wherein, at a surface of an insulating substrate 1, a working electrode 2, a reference electrode 3 and a counter electrode 4 are positioned relative to each other according to a set arrangement, and a gas-permeable proton-conductive film 5 covers these electrodes in such a manner as to form an integrated whole with them.

Entering into details, said insulating substrate 1, for example, is formed of a ceramic material, said working electrode 2 is a thin film electrode of Pt, one of the platinum group metals, said reference electrode 3 is a thin film electrode of Ag, a metal which does not react with flammable gases to be detected or which is free from change of the potential, and said counter electrode 4 is a thin film electrode formed of a material which is in general used for electrodes, each electrode connected with a lead terminal 7 through a wiring pattern 6. Said gas-permeable proton-conductive film 5 is formed of a material (trade-named Nafion, made by Dupont Co.) which is a copolymer of tetrafluoroethylene and perfluorosulfonylfluoride vinyl ether. There is formed a potentiostat circuit by connecting the inverted input terminal of an operational amplifier 8, whose output terminal is connected to the lead terminal of the counter electrode, to the lead terminal of the reference electrode and by connecting the non-inverted input terminal with the earth 10 through a direct current power source 9 (the electromotive force is set at v). By connecting the inverted input terminal of an operational amplifier 11, whose non-inverted input terminal is connected to the earth 10, to the lead terminal of the working electrode, the output terminal connected to the inverted input terminal through a feedback resistance 12 is used as a terminal for drawing signals of the detected concentration.

A flammable-gas sensor constituted as above operates as follows.

When CO gas is introduced as the object of measurement as shown by an arrow A in FIG. 2, the proton-conductive film 5 permits the gas to permeate there through to the working electrode 2 consisting of Pt, at the surface of which, by the catalytic action of Pt, there occurs a reaction expressed by $CO + H_2O \rightarrow CO_2 + 2H^+ + 2e$, whereby proton $H^+$ and electron e are formed. If, then, the proton stays there unremoved, there occurs a reaction expressed by $2H^+ + \frac{1}{2}O_2 + 2e \rightarrow H_2O$, which is considered not to cause an electric current to flow in through the working electrode 2. But the proton moves freely in the proton-conductive film 5 so that the reduction mentioned above is effectively prevented from occurring at the surface of the working electrode 2 and an electric current proportional to the degree of said oxidizing reaction flows in through the working electrode 2. After traversing the proton-conductive film 5, the proton donates itself to the reduction mentioned above at the surface of the counter electrode 4, so that preclusion is accomplished with respect to possibility of protons being present in excess in the proton-conductive film 5, and accordingly, chances are eliminated for the reversible reaction to take place at the surface of the working electrode 2.

Figure 3:
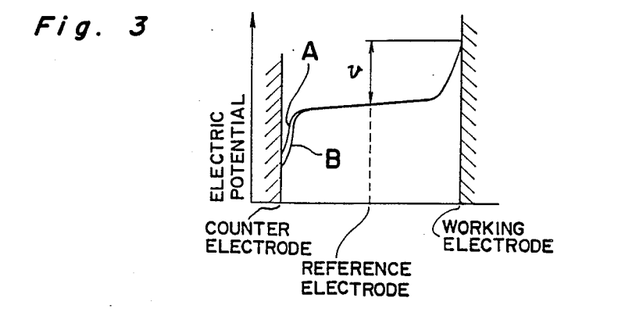
FIG. 3 diagrammatically explains the performance of maintaining the potential difference constant between a working electrode and a reference electrode.

While said oxidation and reduction are taking place, it may occur for the potential of the counter electrode 4 to change, there arising a change of the potential difference between the working electrode 2 and the counter electrode 4. As shown in FIG. 3, however, the potentiostat circuit causes the potential of the reference electrode 3 to automatically change, so that the potential difference between the working electrode 2 and the reference electrode 3 can be maintained at v. Therefore, with the potential at the surface of the working electrode 2 maintained constant, current signals corresponding to the concentrations of the CO gas can be obtained, converted to voltage signals by the operational amplifier 11, and thus signals for the detected CO gas concentrations can be produced with high accuracy.

The description above has dealt with CO gas being introduced on the surface of the working electrode 2. When $H_2$ gas comes in contact with the surface of the working electrode 2, there occur reactions:

so that, in a manner similar to the detection of CO gas, voltage signals corresponding to the concentrations of $H_2$ gas are produced.

Therefore, the concentrations of CO gas and $H_2$ gas in the environment under detection can be measured with high accuracy.

A flammable-gas sensor provided according to the description above can be produced not only in a simple manner by a technique of forming thin films but also with uniformity of a high order in characteristics between products. The characteristics are stabilized over long periods of time while general dimensional reduction and reduction in production cost can be easily accomplished by introducing the sensors hereinbefore described.

Figure 4:
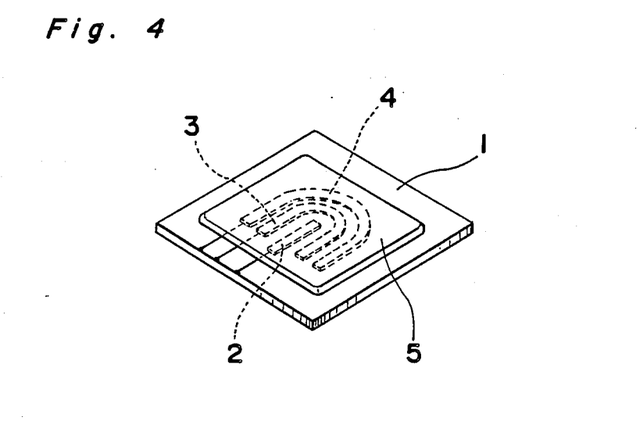
FIGS. 4 through 8 illustrate other embodiments of the present invention, each in a schematic perspective representation.

Referring to FIG. 4, there is shown a flammable-gas sensor as another embodiment in a schematic perspective representation. This sensor differs from the one in FIG. 1 only in that the working electrode 2 is formed in a linear shape, whereas the reference electrode 3 and the counter electrode 4 are in the shape of halves of ellipses.

Accordingly, this embodiment is capable of performance in a manner similar to the performance of the embodiment in FIG. 1.

Describing more particularly, in this embodiment, with the reference electrode 3 positioned between the working electrode 2 and the counter electrode 4 and surrounding the the the greatest part of the working electrode 2, this peculiarity of the arrangement of the electrodes markedly improves the function of the reference electrode 3 to adjust its potential to change of the potential of the counter electrode 4 as compared with the embodiment in FIG. 1, and accordingly a marked improvement is achieved in the accuracy with which the concentrations of flammable gases are measured. Therefore, even when the ionic conductivity of the proton-conductive film 5 is low, the stability, the potential difference between the reference electrode 3 and the working electrode 2, can be improved so as to maintain a high accuracy with respect to measurement of flammable gas concentrations.

Figure 5:
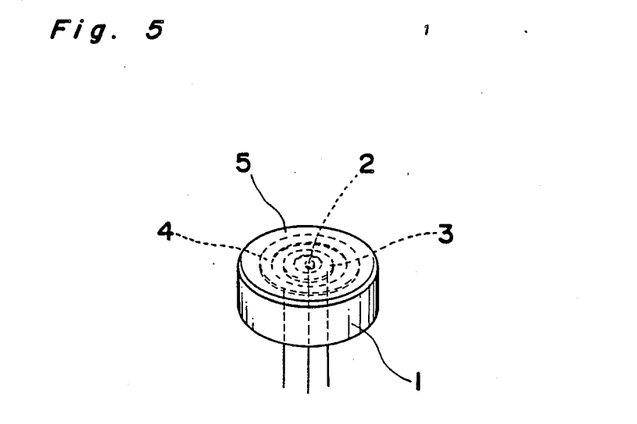

Referring to FIG. 5, there is shown a flammable-gas sensor as another embodiment in a schematic perspective representation. This sensor differs from the embodiments in the foregoing descriptions only in that the reference electrode 3 and the counter electrode 4 are arranged in coaxial circles with the working electrode 2 at the center.

In this embodiment, therefore, a further improvement is accomplished with respect to the follow-up of the potential of the reference electrode 3, and accordingly, in the accuracy with which the concentrations of flammable gases are measured.

In each of the embodiments shown in FIGS. 4 and 5, it is practical for the working electrode 2 to be formed of Au or a platinum group metal other than Pt, for the reference electrode 3 to be formed of a metal other than Ag, such as Pb, which is free from change of the potential in the presence of a flammable gas, and for the proton-conductive film 5 to be formed of antimonic acid, zirconium phosphate, or the like.

As regards to the proton-conductive film 5, it is preferable to use a copolymer of tetrafluoroethylene and perfluorosulfonyl fluoride vinyl ether, as mentioned in the foregoing description of embodiments, especially one obtained by plasma polymerization. Besides the advantages that the polymerization in vacuum reduces the impurities contained and the film is uniform in a quality, the permeability of flammable gases can be adjusted as desired by controlling the thickness of the film and the degree of polymerization.

Figure 6:
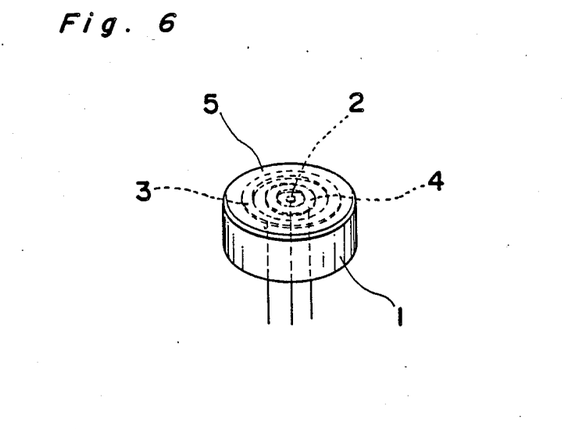

Referring to FIG. 6, there is shown a flammable-gas sensor as another embodiment in a schematic perspective representation. This sensor differs from the embodiment shown in FIG. 5 only in that the reference electrode 3 and the counter electrode 4 are positioned oppositely between the two embodiments.

In this embodiment, too, the potential at the reference electrode 3 changes in accordance with change of the potential at the counter electrode 4, thus voltage signals proportional to the concentrations of flammable gas are output while the potential difference between the working electrode 2 and the reference electrode 3 is maintained at a constant value.

In this embodiment, the performance of follow-up of the potential of a reference electrode 3 is somewhat lowered as compared with the embodiment in FIG. 5, but use of a Pt electrode, which is excellent in electrode characteristics, for the counter electrode counterbalances the lowered follow-up enabling measurement of the flammable gas concentrations with high accuracy.

Figure 7:
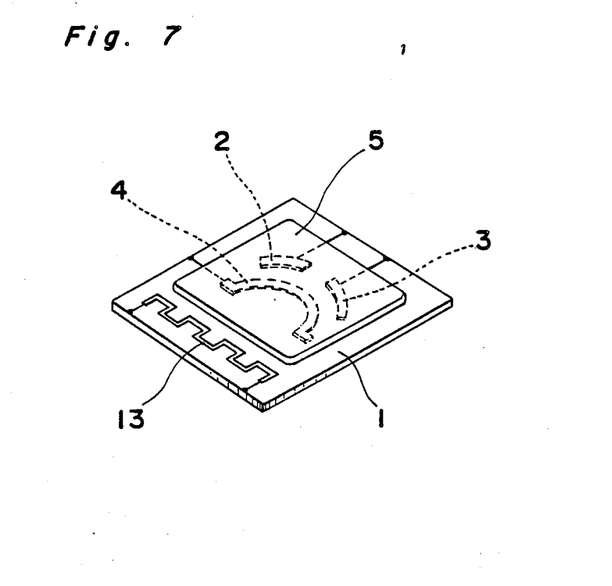

Referring to FIG. 7, there is shown a flammable-gas sensor as another embodiment in a schematic perspective representation. This embodiment differs from the embodiments in the foregoing descriptions only in that there is provided on the insulating substrate 1 a temperature sensor 13 which is formed of Pt in the form of thin film.

This embodiment is capable of detecting temperature by the use of temperature sensor 13, in addition to detecting flammable-gas concentrations. The device, therefore, is useful in a fire alarm system or the like where the alarm is based on both flammable-gas concentration and temperature. Not only is this embodiment provided with a temperature sensor 13, but a signal processing circuit, such as a bridge circuit, can also be incorporated into the sensor system. Although circuits incorporated therein may increase, introduction of a technique on semi-conductor integrated circuits reduces complication of the manufacturing process drastically.

Figure 8:
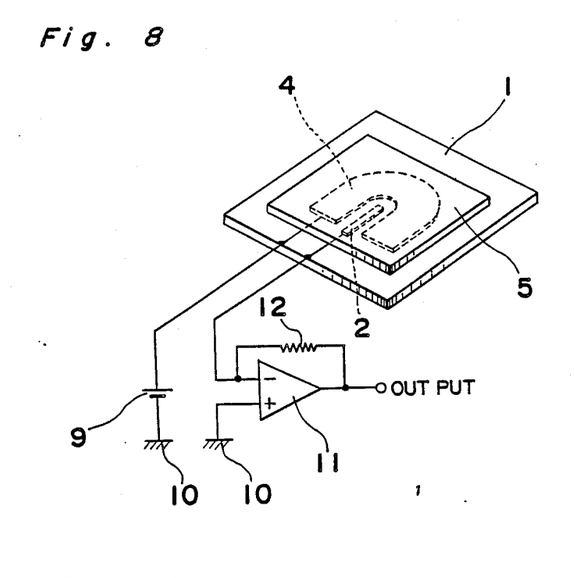

Referring to FIG. 8, there is shown another embodiment in a schematic perspective representation, which differs from the embodiment in FIG. 1 only in that a reference electrode 3 is not used, the counter electrode 4 is approximately 100 times as large in area as the working electrode 2, an operational amplifier 8 is omitted, and a direct current source 9 is connected directly with the counter electrode 4.

This embodiment is characterized by simplified use of electrodes and stabilization of the surface potential of the working electrode resulting from striking enlargement of the counter electrode 4 in area, so that the detection of the flammable-gas concentrations can be done with high accuracy.

The present invention should not be restricted to the above mentioned embodiments. For example, in the flammable-gas sensors shown in FIG. 1 and FIG. 4, the reference electrode 3 and the counter electrode 4 can be positioned, each in the place of the other; and furthermore, each electrode can be set in the insulating substrate 1 in the manner of embedding. Various changes or modifications can be made in adapting the embodiments to particular uses within the scope and spirit of the present invention.

This embodiment according to the present invention consists of only an insulating substrate, at least a working electrode and a counter electrode formed thereon, and a proton-conductive film to cover said electrodes in such a manner as to form an integrated whole with the electrodes, so that the sensor exhibits characteristics showing no irregularities between one another and stability in measurement over long periods of time of use. The embodiment also lends itself to general dimensional reduction and reduction in production cost besides being produced in a simplified process.

Figure 9:
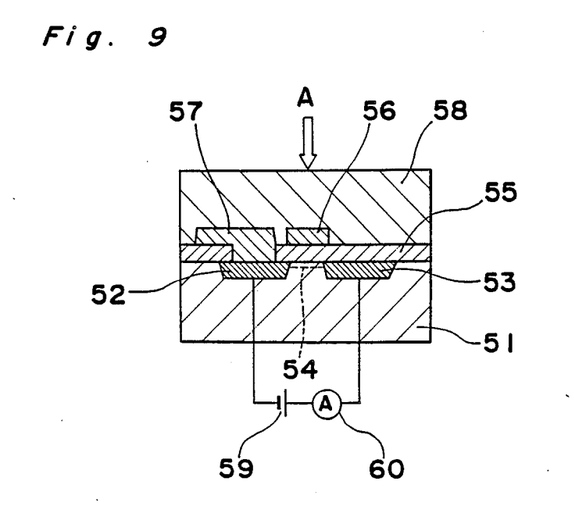
FIG. 9 schematically illustrates another embodiment of the present invention.

Referring to FIG. 9, there is shown schematically a flammable-gas sensor as another embodiment, wherein an n type source region 52 and a drain region 53 are formed at predetermined positions on the surface of a p type substrate 51; an n type channel region 54 is formed between said source region 52 and drain region 53, and except for a part at said source region 52, the surface of said p type substrate 51 is entirely covered with an insulating film 55. Further, there is formed a gate electrode 56 of platinum on said insulating film 55 at the position opposite to that of said channel region. Also, is formed a source electrode 57 of silver in such a manner as to be in contact with said source region 52 and a solid electrolyte film 58 serving a gas-permeable, proton-conductive film formed so as to cover said gate electrode 56, source electrode 57 and insulating film 55. Numeral 59 denotes a direct current power source and 60 an ammeter, both of which are connected in series and arranged between said source region 52 and drain region 53.

A flammable-gas sensor constituted as above operates as follows.

When hydrogen gas is introduced as the object of measurement as shown by an arrow A in FIG. 9, the gas permeates through the solid electrolyte film 58 to the gate electrode 56 formed of platinum, and then undergoes, at the surface of the gate electrode 56 by the catalytic action of platinum, reactions expressed as $$H_2 \rightarrow 2H^+ + 2e$$

$$2H^+ + \tfrac{1}{2}O_2 + 2e \rightarrow H_2O$$

Figure 10A:
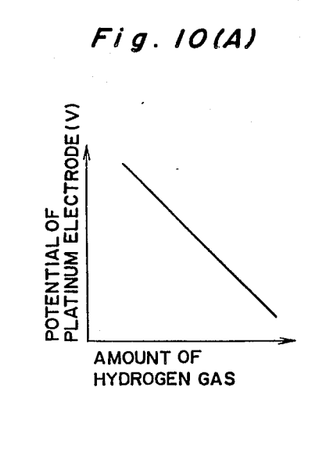
FIGS. 10(A), (B) and (C) schematically show characteristics describing the performance of the embodiment shown in FIG. 9.

Said reversible reaction does not occur frequently because $H^+$ ions move freely in the solid electrolyte film 58, while the gate electrode 56 assumes a deep negative potential (see FIG. 10(A)) as hydrogen gas which permeates through the solid electrolyte film 58 to the gate electrode 56 increases.

Figure 10B:
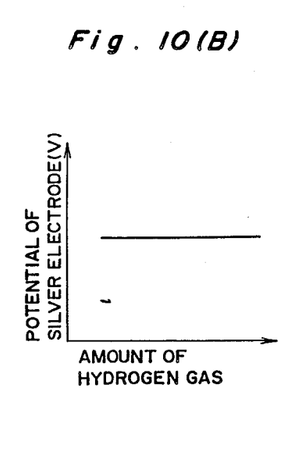

On the other hand, the source electrode 57, the silver not reacting to hydrogen gas, continues to maintain a set potential (see FIG. 10(B)) irrespective of the change of the concentration of the hydrogen gas.

Figure 10C:
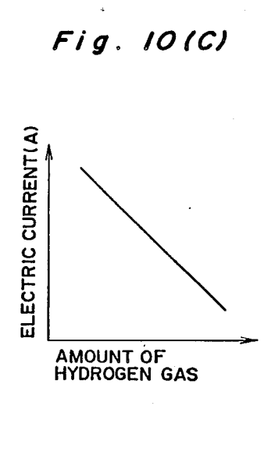

Accordingly, a potential corresponding to the concentration of the hydrogen gas is formed between the source electrode and gate electrode, and when a set voltage is applied between the source electrode and drain electrode, a current characteristic showing a decrease is seen as the concentration of the hydrogen gas increases (see FIG. 10(C)).

Since $H^+$ ions generated at or near the gate electrode 56 when said performance is taking place, are reserved without being wasted, there is no need of using a measuring instrument with an especially high impedance, since by using an ordinary ammeter the concentration of hydrogen gas can be measured accurately.

The above description has dealt with hydrogen gas. The measurement of the concentration of carbon monoxide gas can be carried out in a similar manner.

Carbon monoxide gas also undergoes a reversible reaction as does hydrogen gas as follows:

$$CO + H_2O \rightarrow CO_2 + 2H^+ + 2e$$

$$2H^+ + \tfrac{1}{2}O_2 + 2e \rightarrow H_2O$$

Accordingly, the electron generated in the above reaction is used to measure concentrations of carbon monoxide gas.

Figure 11:
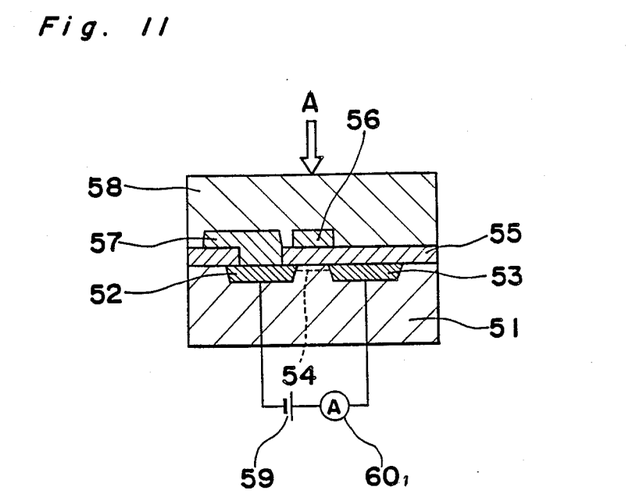
FIG. 11 schematically illustrates another embodiment of the present invention.

Referring to FIG. 11, there is shown schematically another embodiment, which differs from the above described embodiment only in that the gate electrode 56 is formed of silver and the source electrode 57 is formed of platinum.

Figure 12:
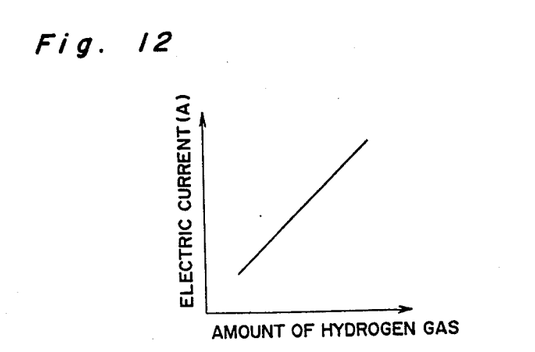
FIG. 12 diagrammatically shows a characteristic of the embodiment shown in FIG. 11.

Accordingly, the potential of the gate electrode 56 is maintained at a set value irrespective of the concentration of the hydrogen gas, whereas the source electrode 57 assumes a deep negative potential as the concentration of the hydrogen gas increases. A potential which depends on the concentration of hydrogen gas and which changes inversely as compared with the above mentioned embodiment is formed between the source electrode and gate electrode, and when a set voltage is applied between the source electrode and gate electrode, a current characteristic showing an increase is seen as the concentration of the hydrogen gas increases (see FIG. 12).

The present invention should not be restricted to the above mentioned embodiments. For example, a calomel electrode can be substituted for a silver electrode and a metal of the platinum group, other than platinum, can be substituted for a platinum electrode. The gas permeability of the solid electrolyte film 58 can be changed so as to change the range of the measurement and a plurality of flammable-gas sensors whose ranges of measurement have been changed can be arranged in parallel and selectively operated by switches. Various changes or modifications can be made in adapting the embodiments to particular uses within the scope and spirit of the present invention.

As is obvious from the above description, according to the present invention, a field-effect transistor is formed by using an electrode, which reacts to flammable gases, and an electrode, which does not react to flammable gases. Since the surface of the field-effect transistor is covered with a gas-permeable, proton-conductive film, concentrations of flammable gases can be measured accurately without involving the danger of a gas explosion.

ADVANTAGES OF THE INVENTION

The surface of a flammable-gas sensor, provided by the present invention, is covered with a gas-permeable, proton-conductive film. This feature assuredly eliminates the danger of gas explosion from the use of a flammable gas sensor, and also helps to introduce compact models and to reduce the production cost. Measurement of the concentrations of flammable gases can be carried out with accuracy. The sensors provided according to the present invention, therefore, can be used advantageously in fire alarm systems and in chemical industry.

What is claimed is:

1. A flammable-gas sensor comprising:
an insulating substrate,
a working electrode provided at the surface of said insulating substrate,
a counter electrode provided at a surface of said insulating substrate and positioned with a set gap from said working electrode, and
a gas permeable, proton-conductive film which covers said working electrode and counter electrode and forms an integrated whole with said working electrode and counter electrode,
wherein said counter electrode is larger in area than said working electrode by a factor of 10 or more.

2. A flammable-gas sensor comprising:
an insulating substrate,
a working electrode provided at a surface of said insulating substrate,
a counter electrode provided at the surface of said insulating substrate and positioned with a set gap from said working electrode,
a reference electrode provided at the surface of said insulating substrate and positioned with set gaps from said working electrode and counter electrode, and
a gas permeable, proton-conductive film which covers said working electrode, counter electrode and reference electrode and forms an integrated whole with said working electrode, counter electrode and reference electrode,
wherein said reference electrode and counter electrode form coaxial circles with said working electrode at the center.

3. A flammable-gas sensor comprising:
an insulating substrate,
a working electrode provided at a surface of said insulating substrate,
a counter electrode provided at the surface of said insulating substrate and positioned with a set gap from said working electrode,
a reference electrode provided at the surface of said insulating substrate and positioned with set gaps from said working electrode and counter electrode, and
a gas permeable, proton-conductive film which covers said working electrode, counter electrode and reference electrode and forms an integrated whole with said working electrode, counter electrode and reference electrode,
wherein said reference electrode is positioned between said working electrode and counter electrode.

* * * * *